United States Patent
Flohr et al.

(10) Patent No.: US 6,551,436 B1
(45) Date of Patent: Apr. 22, 2003

(54) METHOD FOR FORMING AN APERTURED WEB

(75) Inventors: Andreas Flohr, Mulheim/Ruhr (DE); Georg Pescher, Bad Soden (DE)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 09/806,889

(22) PCT Filed: Oct. 6, 1999

(86) PCT No.: PCT/US99/23299

§ 371 (c)(1),
(2), (4) Date: Apr. 5, 2001

(87) PCT Pub. No.: WO00/23024

PCT Pub. Date: Apr. 27, 2000

(30) Foreign Application Priority Data

Oct. 16, 1998 (EP) .............................................. 98119550

(51) Int. Cl.[7] .............................................. D06C 27/00
(52) U.S. Cl. .................. 156/251; 156/88; 156/252; 156/253; 156/270; 156/269; 156/308.4; 156/513; 156/514; 156/515; 156/530; 156/582; 225/103; 225/93
(58) Field of Search .................. 156/251, 252, 156/253, 270, 269, 88, 514, 513, 515, 530, 308.4, 582; 83/15, 30; 100/160, 170, 38, 39; 408/1 R, 241 R; 225/3, 4, 94, 103, 93; 28/299; 428/131

(56) References Cited

U.S. PATENT DOCUMENTS

| | | | |
|---|---|---|---|
| 4,047,531 A | 9/1977 | Karami | 604/374 |
| 4,704,112 A | 11/1987 | Suzuki et al. | 604/378 |
| 4,758,297 A | 7/1988 | Calligarich | 156/251 |
| 4,798,603 A | 1/1989 | Meyer et al. | 604/378 |
| 4,892,536 A | 1/1990 | DesMarais et al. | 604/385.27 |
| 4,909,803 A | 3/1990 | Aziz et al. | 604/385.28 |
| 4,968,312 A | 11/1990 | Khan | 604/385.13 |
| 4,990,147 A | 2/1991 | Freeland | 604/385.22 |
| 5,037,409 A | 8/1991 | Chen et al. | 604/358 |
| 5,037,416 A | 8/1991 | Allen et al. | 604/358.22 |
| 5,062,840 A | 11/1991 | Holt et al. | 604/385.19 |
| 5,124,197 A | 6/1992 | Bernardin et al. | 442/35 |
| 5,134,007 A | 7/1992 | Reising et al. | 428/78 |
| 5,147,343 A | 9/1992 | Kellenberger | 604/368 |
| 5,149,335 A | 9/1992 | Kellenberger et al. | 210/773 |
| 5,171,236 A | 12/1992 | Dreier et al. | 604/369 |
| 5,342,338 A | 8/1994 | Roe | 604/383 |
| 5,628,097 A * | 5/1997 | Benson et al. | 28/165 |
| 5,704,101 A | 1/1998 | Majors et al. | 26/18.6 |
| 6,166,285 A | 12/2000 | Schulte et al. | 604/364 |

FOREIGN PATENT DOCUMENTS

| | | |
|---|---|---|
| EP | 0 355 740 B1 | 2/1990 |
| WO | WO 97/11662 A1 | 4/1997 |

OTHER PUBLICATIONS

PCT International Search Report for PCT/US99/23299, date of mailing: Feb. 4, 2000.

* cited by examiner

*Primary Examiner*—Linda Gray
(74) *Attorney, Agent, or Firm*—Jeffrey R. Moore; Jay A. Krebs; Ken K. Patel (57) ABSTRACT

A method for forming an apertured web which may be used as a topsheet on a disposable absorbent article, such as a diaper. The web (240) is fed in as machine direction through a first nip (250) formed by a pair of rollers one of the rollers having a smooth outer surface and the other roller having an outer surface with a plurality of projections extending from it's outer surface. At least one of the rollers of the first nip (250) is heated. The first nip (250) apertures the web with a plurality of apertures each having a fused perimeter. The web (240) is then cooled to solidify the fused perimeter of the apertures. The web (240) is then fed through a second nip (280) formed by a pair of rollers to break the solidified fused perimeter of the apertures. One of the rollers of the second nip (280) has an outer surface with a plurality of grooves.

9 Claims, 5 Drawing Sheets

METHOD FOR FORMING AN APERTURED WEB

FIELD OF THE INVENTION

This invention relates to a method for forming an apertured web, and more particularly to a method for forming an apertured web suitable for use as a topsheet on a disposable absorbent article.

BACKGROUND OF THE INVENTION

Disposable absorbent articles such as diapers and adult incontinence products are well known in the art. Such disposable absorbent articles collect and retain urine and fecal material deposited thereon by the wearer.

To date, most attempts in the art to handle the urine and fecal material collected and retained in the disposable absorbent article have been directed to handling urine. Dealing with fecal material collected by the disposable absorbent article is simply more difficult than dealing with urine, due to the complex rheology of low-viscosity fecal material.

Exemplary of the urine handling prior art are several attempts to provide disposable absorbent articles having a first topsheet which faces towards and contacts the body of the wearer, and a secondary topsheet under the first topsheet, which either absorbs urine, or transfers the urine to an underlying core for storage until the disposable absorbent article is removed from the wearer.

Typically, the first topsheet and secondary topsheet have different material properties. The secondary topsheet may have a smaller pore size than the first topsheet, to assist in transfer of the urine through the topsheet. The first topsheet may be hydrophobic and more resilient when wetted than the secondary topsheet, in order to pass fluids through the first topsheet to the secondary topsheet.

In yet another attempt in the prior art, the disposable absorbent article has a first topsheet, secondary topsheet and core. The secondary topsheet consists essentially of melt-blown hydrophilic fibers and has a pore size greater than the pore size of the core. This arrangement allegedly allows the secondary topsheet to rapidly receive multiple liquid insults and distribute the liquid in the X-Y plane prior to absorption by the core. In yet another attempt, improved vertical wicking capability for urine has been allegedly achieved using inflated cellulose fibers which are free of a surface finish or are crosslinked to one another.

In another attempt in the prior art, an absorbent core suitable for acquiring and containing liquids such as urine in a particularly effective and efficient manner comprises multiple layers. The first layer, which is closest to the wearer, comprises hydrophilic fibrous material and has an acquisition zone of a relatively lower average density than other portions of this layer, in order to quickly acquire discharged liquids. Below the first layer is a liquid handling layer comprising a resilient, low density high void volume material that is moisture insensitive in order to rapidly acquire liquid insults into itself through the acquisition zone and distribute these liquids throughout the liquid handling layer to a storage layer. The storage layer comprises a combination of fibrous material and discrete particles of absorbent gelling material, and allows the liquid handling layer to be drained of the liquids it has acquired, so that the liquid handling layer may have sufficient capacity to acquire and distribute subsequent loadings of liquids.

Examples of such attempts in the prior art include U.S. Pat. No. 4,047,531 issued Sep. 13, 1977 to Karami; U.S. Pat. No. 4,798,603 issued Jan. 17, 1989 to Meyer et al.; U.S. Pat. No. 5,037,409 issued Aug. 6, 1991 to Chen et al.; U.S. Pat. No. 5,124,197 issued Jun. 23, 1992 to Bernardin et al.; and U.S. Pat. No. 5,134,007 issued Jul. 28, 1992 to Reising et al.

Of course, absorbent gelling materials are also now well known in the prior art for their urine handling capability. Absorbent gelling materials are polymeric materials capable of absorbing large quantities of fluids, such as urine, and retaining such absorbed fluids under moderate pressure. The effectiveness of the absorbent gelling materials is quite dependent upon the form, position, and weight percentage of the absorbent gelling materials which are incorporated into the core of the disposable absorbent article.

Recent attempts have been made in the art to provide absorbent gelling materials which have the ability to swell against pressure. These teachings allege to provide the advantage that the absorbent gelling materials absorb fluid under actual pressures exerted by the body during use. Yet other teachings in the art provide absorbent gelling materials having a particular free swell rate and absorbency under load. Alleged advantages of such an absorbent gelling materials are lower volume and mass with approximately the same absorbent capacity, the ability to rapidly absorb a discharged liquid under pressures typically encountered during use, and the ability to retain the absorbed liquid under pressures typically encountered during use.

In another prior attempt, U.S. Pat. No. 4,704,112 issued to Suzuki et al. discloses a facing comprising a nonwoven fabric having two different layers of different fiber compositions. The upper layer has a pattern of apertures therein and is made from hydrophobic fibers and the lower layer has no apertures and is made from hydrophilic fibers.

Examples of such attempts in the prior art include U.S. Pat. No. 5,147,343 issued Sep. 15, 1992 to Kellenberger and U.S. Pat. No. 5,149,335 issued Sep. 22, 1992 to Kellenberger et al.

However, all of these attempts to handle urine do little, if anything, to improve handling of low-viscosity fecal material which may also be present in the disposable absorbent article. Attempts to deal with fecal material include providing a first topsheet which conforms closely to the wearer and has an aperture. The aperture is hopefully registered with the anal opening, so that fecal material passes therethrough into a void space. The first topsheet may comprise various elastic panels in order to closely conform to the skin of the wearer, and/or may have linear elastic strands. Improvements have been made in this area of the prior art, such as optimizing the material properties of the first topsheet. Such optimization makes the first topsheet more comfortable to the wearer and allows a single disposable absorbent article to fit a larger range of sizes of wearers.

Yet other attempts have been made in this area of the prior art to provide an absorbent core with a hole therein, in order to receive the fecal material. The hole may be oblate shaped, so that it is longer and narrower than the aperture in the first topsheet, or may be diamond shaped. The hole in the core may be positioned below an aperture which has elastic strips around its edge.

Improvements to this genre of the prior art disposable absorbent articles also include the addition of spacers. Spacers may be interposed between the first topsheet and the core, in order to ensure a void space is present to receive the fecal material.

Yet other attempts have been made in this genre of the prior art to provide barriers which limit the movement of fecal material to particular portions of the disposable absorbent article. The barriers limit the contact of the fecal material to a lesser portion of the skin of the wearer, than a comparable disposable absorbent article which has no barriers.

Still other attempts in the prior art provide barrier leg cuffs which are upstanding from the plane of the topsheet. The barrier leg cuffs prevent fecal material from breaching the perimeter of the disposable absorbent article.

Examples of such attempts to handle fecal material include U.S. Pat. No. 4,892,536 issued Jan. 9, 1990 to DesMarais et al.; U.S. Pat. No. 4,909,803 issued Mar. 20, 1990 to Aziz et al.; U.S. Pat. No. 4,968,312 issued Nov. 6, 1990 to Khan; commonly assigned U.S. Pat. No. 4,990,147 issued Feb. 5, 1991 to Freeland; commonly assigned U.S. Pat. No. 5,037,416 issued Aug. 6, 1991 to Allen et al.; U.S. Pat. No. 5,062,840 issued Nov. 5, 1991 to Holt et al.; commonly assigned U.S. Pat. No. 5,171,236 issued Dec. 15, 1992 to Dreier et al.; and European Patent Application 0,355,740 A2 published Feb. 28, 1990 to Enloe.

However, none of these attempts to handle fecal material solve the problem of low-viscosity fecal material which is predominately prevalent in younger children, particularly those who are breast fed. Low-viscosity fecal material easily migrates within the disposable absorbent article under the influences of gravity and motion or pressure by the wearer.

The migration of the fecal material often moves it towards the perimeter of the disposable absorbent article, increasing the likelihood of leakage. The migration of the fecal material also smears it against the skin of the wearer, making cleanup more difficult. In order to clean the wearer, the caretaker must wipe the entire area of the skin which has encountered the fecal material and typically has to deal with a relatively large soiled area.

One attempt in the art to handle low-viscosity fecal material is found in U.S. Pat. application Ser. No. 08/076,713 filed Jun. 11, 1993 in the name of Roe. This application is a disposable absorbent article having a first topsheet with a high trans-topsheet penetration overlaying a secondary topsheet having a lesser trans-topsheet penetration.

BRIEF SUMMARY OF THE INVENTION

The invention is a method for forming an apertured web which may be used as a topsheet on a disposable absorbent article, such as a diaper. The web is fed in a machine direction through a first nip formed by a pair of rollers one of the rollers having a smooth outer surface and the other roller having an outer surface with a plurality of projections extending from it's outer surface. At least one of the rollers forming the first nip is heated, preferably both rollers are heated. As the web passes through the first nip a plurality of apertures are created each having a fused perimeter. The web is cooled to solidify the fused perimeter of the apertures. The web is then fed through a second nip formed by a pair of rollers to break the solidified fused perimeter of the apertures. One of the rollers of the second nip has an outer surface comprising a plurality of grooves.

The web may be fed through a third nip formed by a pair of rollers to further break the fused perimeter of the apertures. One of the rollers of the third nip has an outer surface comprising a plurality of grooves.

BRIEF DESCRIPTION OF THE DRAWINGS

While the specification concludes with claims pointing out and distinctly claiming the present invention, it is believed the same will be better understood by the following drawings taken in conjunction with the accompanying specification wherein like components are given the same reference number.

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner.

Figure 1:
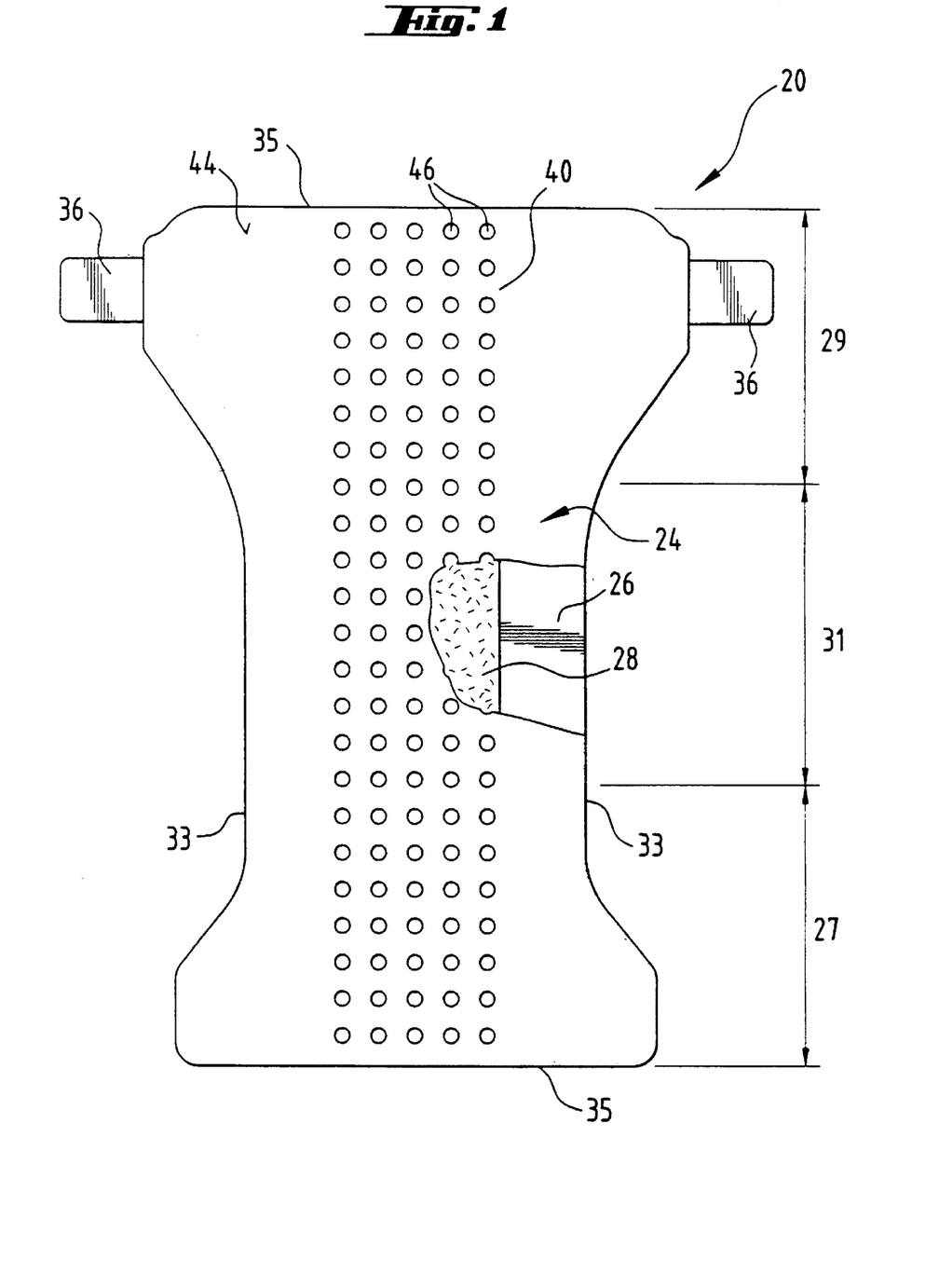
FIG. 1 is a top plan view, shown partially in cutaway, of a disposable diaper having a topsheet constructed of the apertured web of the present invention.

An absorbent article utilizing the apertured web of the present invention as a topsheet thereon is the unitary disposable absorbent article, diaper 20, shown in FIG. 1. As used herein, the term "diaper" refers to an absorbent article generally worn by infants and adult incontinent persons and is worn about the lower torso of the wearer. The web of the present invention may also be used as a topsheet on other absorbent articles such as incontinence briefs, incontinence undergarments, absorbent inserts, diapers holders and liners, feminine hygiene garments, and the like.

While the present invention will be described in the context of providing a web suitable for use as a topsheet on a disposable absorbent article, the present invention is in no way limited to such application. The description of the apertured web and its use as a topsheet will allow one skilled in the art to readily adapt the invention to other devices and for other uses.

FIG. 1 is a plan view of the diaper 20 of the present invention in its flat-out, uncontracted state (i.e., with elastic induced contraction pulled out) with portions of the structure being cut-away to more clearly show the construction of the diaper 20 and with the portion of the diaper 20 which faces or contacts the wearer, the inner surface, oriented towards the viewer. As shown in FIG. 1, the diaper 20 preferably comprises a liquid pervious topsheet 24; a liquid impervious backsheet 26 joined with the topsheet 24; and an absorbent core 28 intermediate the topsheet 24 and the backsheet 26. The diaper 20 may further comprise elasticized side panels (not shown); elasticized leg cuffs (not shown); an elastic waist feature (not shown); and a fastening system with tape tabs generally multiply designated as 36.

The diaper 20 is shown in FIG. 1 to have a first waist region 27 juxtaposed with the front of the wearer while the diaper 20 is being worn, a second waist region 29 opposed to the first waist region 27 and juxtaposed with the back of the wearer while the diaper 20 is being worn, a crotch region 31 positioned between the first waist region 27 and the second waist region 29, and a periphery which is defined by the outer edges of the diaper 20 in which the longitudinal edges are designated 33 and the end edges are designated 35. The inner surface of the diaper 20 comprises that portion of the diaper 20 which is adjacent to the wearer's body during use (i.e., the inner surface generally is formed by at least a portion of the topsheet 24 and other components joined to the topsheet 24). The outer surface comprises that portion of the diaper 20 which is positioned away from the wearer's body (i.e., the outer surface generally is formed by at least a portion of the backsheet 26 and other components joined to the backsheet 26) during use.

FIG. 1 shows an embodiment of the diaper 20 in which the topsheet 24 and the backsheet 26 have length and width dimensions generally larger than those of the absorbent core 28. The topsheet 24 and the backsheet 26 extend beyond the edges of the absorbent core 28 to thereby form the periphery of the diaper 20. While the topsheet 24, the backsheet 26, and the core 28 may be assembled in a variety of well known configurations, preferred diaper configurations are described generally in U.S. Pat. No. 3,860,003 entitled "Contractable Side Portions for Disposable Diaper" which issued to Kenneth B. Buell on Jan. 14, 1975; and U.S. Pat. No. 5,151,092, "Absorbent Article With Dynamic Elastic Waist Feature Having A Predisposed Resilient Flexural Hinge", issued to Kenneth B. Buell et al. Sep. 29, 1992; each of which is incorporated herein by reference.

The absorbent core 28 may be any absorbent means which is generally compressible, conformable, non-irritating to the wearer's skin, and capable of absorbing and retaining liquids such as urine and other certain body exudates. As shown in FIG. 1, the absorbent core 28 has a garment surface, a body surface, side edges, and waist edges. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 28 may also be varied (e.g., the absorbent core 28 may have varying caliper zones, a hydrophilic gradient, a superabsorbent gradient, or lower average density and lower average basis weight acquisition zones; or may comprise one or more layers or structures). The total absorbent capacity of the absorbent core 28 should, however, be compatible with the design loading and the intended use of the diaper 20. Further, the size and absorbent capacity of the absorbent core 28 may be varied to accommodate wearers ranging from infants through adults.

Exemplary absorbent structures for use as the absorbent core 28 are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. 4,834,735, entitled "High Density Absorbent Members Having Lower Density and Lower Basis Weight Acquisition Zones", issued to Alemany et al. on May 30, 1989. Each of these patents is incorporated herein by reference.

The backsheet 26 is positioned adjacent the garment surface of the absorbent core 28 and is preferably joined thereto by attachment means (not shown) such as those well known in the art. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element.

For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola et al. on Mar. 4, 1986, more preferably several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents is incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body.

The backsheet 26 prevents the exudates absorbed and contained in the absorbent core 28 from wetting articles which contact the diaper 20 such as bedsheets and undergarments. The backsheet 26 may thus comprise a woven or nonwoven material, polymeric films such as thermoplastic films of polyethylene or polypropylene, or composite materials such as a film-coated nonwoven material. Preferably, the backsheet 26 is a thermoplastic film having a thickness of about 0.012 mm (0.5 mil) to about 0.051 mm (2.0 mils). Particularly preferred materials for the backsheet 26 include RR8220 blown films and RR5475 cast films as manufactured by Tredegar Industries, Inc. of Terre Haute, Ind. The backsheet 26 is preferably embossed and/or matte finished to provide a more clothlike appearance. Further, the backsheet 26 may permit vapors to escape from the absorbent core 28 (i.e., be breathable) while still preventing exudates from passing through the backsheet 26.

The topsheet 24 is juxtaposed with, but not necessarily adjacent the body surface of the absorbent core 28, and is preferably joined to the backsheet 26 or absorbent core 28 by means such as those well known in the art. Suitable attachment means are described above with respect to joining the backsheet 26 to the absorbent core 28. In a preferred embodiment of the present invention, the topsheet 24 and the backsheet 26 are joined directly to each other in the diaper periphery.

Figure 2:
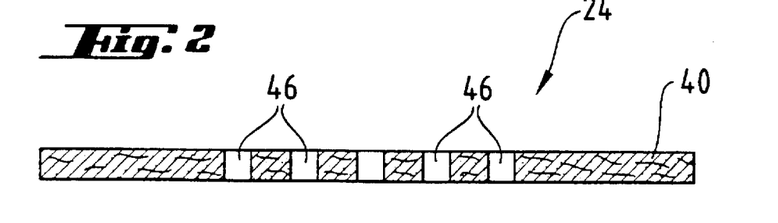
FIG. 2 is a cross-sectional view of the apertured web topsheet shown in FIG. 1.

Referring now to FIGS. 1 and 2, the topsheet 24 comprises a web 40 constructed of a liquid pervious material. The web 40 is compliant, soft feeling, and non-irritating to the wearer's skin. The web 40 is preferably a liquid pervious nonwoven web. The nonwoven web is a fibrous material formed from fusible polymeric fibers or filaments. The nonwoven web can be formed from any of the following polymers: polyamides, polypropylene, polypropylene copolymers, bi-component, polyethylene, polyethylene-terephthalate, combinations thereof, and the like. Suitable materials include dry laid and carded webs, air laid and random webs, spunbonded webs, meltblown webs, spun-laced webs, and through-air or calendar bonded webs. Alternatively, the nonwoven web can be latex-bonded via saturation bonding, gravure printing, screen printing, spray or foam bonding. Still further, the nonwoven web may be bonded with combinations of the above techniques, such as latex bonded and calendar bonded webs or other suitable combinations. The fibers can be of various sizes with fibers having a denier between about 1 and 18 being preferred. The web 40 preferably has a basis weight of from about 5 gsm to 100 gsm, more preferably of from about 5 gsm to about 60 gsm. The web 40 preferably has a caliper of from about 0.1 mm to 5.0 mm, and more preferably of from about 0.1 mm to about 2.0 mm.

The web 40 has a plurality of apertures 46 with an effective aperture size of at least 0.2 square millimeters, more preferably, the plurality of apertures have an effective aperture size of at least 0.5 square millimeters, even more preferably, the plurality of apertures have an effective aperture size of at least 1.0 square millimeter, and most preferably, the plurality of apertures have an effective aperture size of at least 2.0 square millimeters. Effective apertures are those which have a gray level of 18 or less on a standard gray level scale of 0–255, under the image acquisition parameters described below.

The web 40 preferably has an effective open area of at least 10 percent, more preferably the web 40 has an effective open area of at least 15 percent, even more preferably, the web 40 has an effective open area of at least 20 percent, and most preferably the web 40 has an effective open area of at least 25 percent.

The effective aperture size and effective open area are determined by the following procedure using the image analysis described below. The procedure has three principal steps: image acquisition, i.e., obtaining representative images of areas on the surface of the web 40; image measurement, i.e., measuring the percentage open area of an image and of individual apertures and their perimeters; and data analysis, i.e., exporting the percentage open area, individual aperture area, and perimeter measurements to a spreadsheet where frequency distributions, sum of area distributions, and hydraulic radius computations are made.

An image analysis system having a frame grabber board, microscope, camera and image analysis software is utilized. A model DT2855 frame grabber board available from Data Translation of Marlboro, Mass. is provided. A VH5900 monitor microscope, a video camera, having aVH50 lens with a contact type illumination head available from the Keyence Company of Fair Lawn, N.J. are also provided and used to acquire an image to be saved to computer file. The Keyence microscope acquires the image and the frame grabber board converts the analog signal of this image into computer readable digital format. The image is saved to computer file and measured using suitable software such as the Optimas Image Analysis software, version 3.1, available from the BioScan Company of Edmaons, Wash. In order to use the Optimas Image Analysis software, the computer should have Windows software, version 3.0 or later, available from the Microsoft Corporation of Redmond, Wash. And also have a CPU at least equivalent to the Intel 80386. Any suitable desk top PC may be used, with a 486 DX33 type PC having been found to be particularly suitable. Images being saved to and recalled from file were displayed on a Sony Trinitron monitor model PVM-1343MO with a final display magnification of about 50×.

The image acquisition step, noted above requires 10 different regions from a representative sample of material to be tested. Each region is rectangular, measuring about 5.8 millimeters by 4.2 millimeters. The sample is placed on a black mat board to increase the contrast between the apertures and the portion of the sample which defines the apertures. The mean gray level and standard deviation of the black mat board were 16 and 4, respectively.

Images are acquired with room lights off using the Keyence monitor microscope mounted on a copystand directly above the sample. The Keyence light source illuminating the sample is adjusted and monitored with the Optimas software to measure the mean gray level and standard deviation of a 0.3 density wedge on a Kodak Gray Scale available from Eastman Kodak Company of Rochester, N.Y. The control of Keyence light source is adjusted so that the mean gray level of the illuminated wedge is 111±1 and the standard deviation is 10±1. All images were acquired during a single time period, and the Keyence light source is monitored by measuring the mean gray level and standard deviation of the wedge throughout the image acquisition process.

In measuring an individual aperture, only the effective aperture size is of interest. Measuring the effective aperture size quantifies the aperture size intended to contribute to the porosity of the material, and account for contributions of fibers and fiber bundles which traverse an area intended to be an aperture. An effective aperture is any hole through the material having a gray level less than or equal to 18 using image acquisition parameters as described herein. Thus, an intended aperture may be divided into plural effective apertures by traverse fibers.

The image analysis software is calibrated in millimeters by a ruler image acquired from the sample images. A 3 by 3 pixel averaging filter found in the Optimas 3.1 Image menu is applied to each saved image to reduce noise. The apertures are detected in the gray level range of 0 through 18. An aperture which is not fully contained within the 5.8 by 4.2 viewing area is not considered in the individual area and perimeter measurements. Therefore, area and perimeter averages and distributions are not affected by apertures which are not wholly contained within the field of view.

However, individual apertures which could not be fully viewed in the image are included in the percentage open area calculation. This difference occurs because the percent open area is simply the image of pixel ratios from 0 through 18 to the total number of pixels in the image. Areas having a gray level 19 or greater were not counted in the open area calculation.

The percentage open area for the average of 10 images for each material is measured using the Optimas Image Analysis software. The percentage open area is defined as the ratio of the number of pixels having a gray level from 0 through 18 to the total number of pixels for the image. The percentage open area is measured for each image representing one particular region from a sample. The percentage open area from each of the 10 individual images is then averaged to yield a percentage open area for the entire sample.

The data analysis is conducted by an Excel spreadsheet, also available from the Microsoft Corporation of Redmond, Wash. The Excel spreadsheet organized the percentage open area, aperture area, and aperture perimeter measurements obtained from the Optimas software. Sample averages and standard deviations, size and frequency distributions of individual aperture areas and hydraulic radius computations (area divided by perimeter) for individual apertures are obtained using the spreadsheet.

Distributions of individual aperture area are also computed using the Excel spreadsheet. The apertures are sorted into bins of certain size ranges. The number of aperture areas falling into certain size ranges of interest is determined as well as the sum of the areas within each range. The ranges are set in increments of 0.05 square millimeters. These areas are expressed as a percentage of the total open area of the sample. The frequency and sum of the area distributions are obtained by combining individual aperture measurements from all 10 images for each sample.

The apertures 46 in the web 40 can vary in size, shape and pattern. Examples of some possible shapes include but are not limited to circular, square, rectangular, oval, triangular, dog-bone, star, oblong, etc. The apertures 46 can be arranged in either a systematic, uniform or random pattern. A systematic pattern, with similarly sized apertures is preferred.

Figure 3:
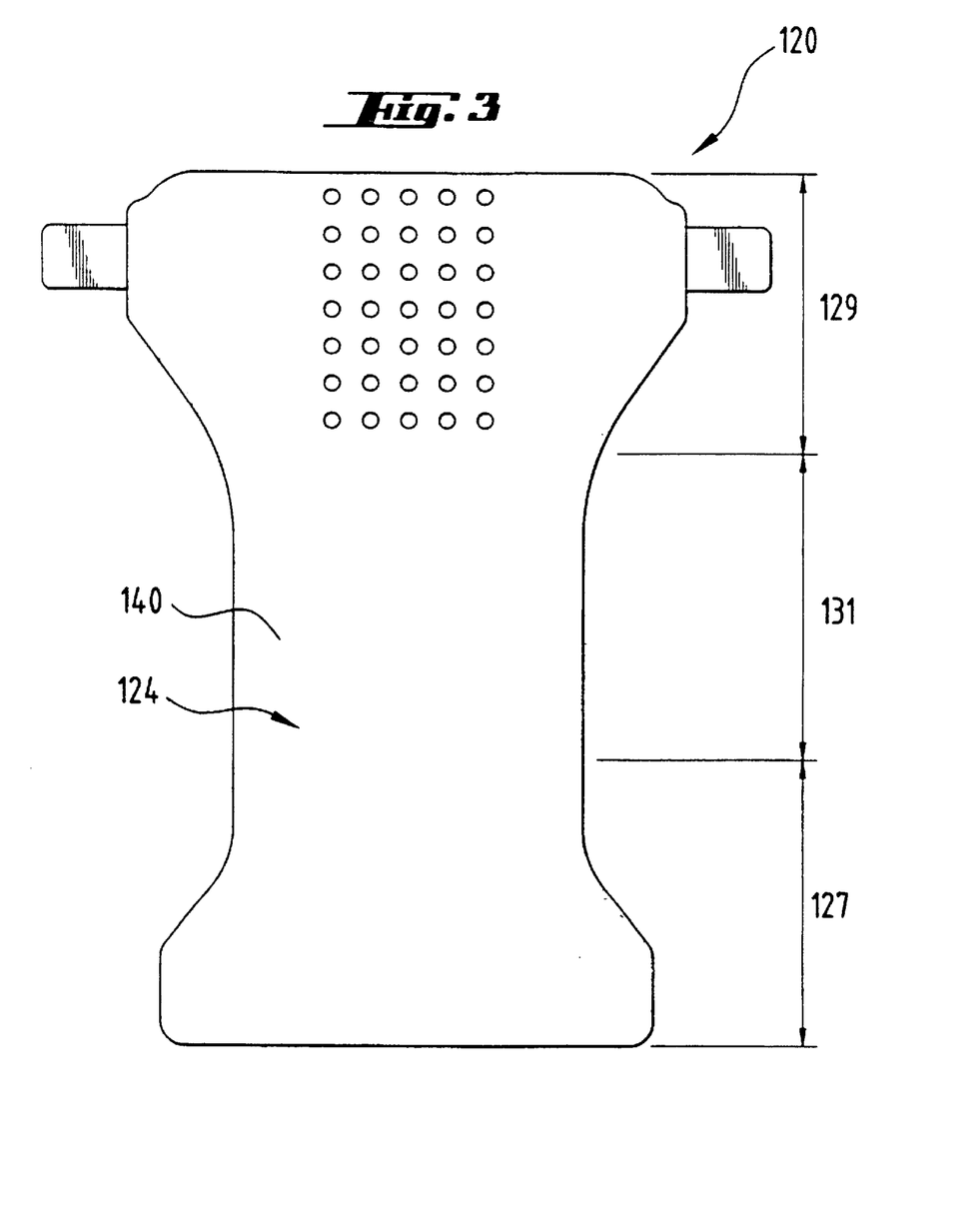
FIG. 3 is a top plan view of a disposable diaper having a topsheet constructed of another embodiment of the web of the present invention.

Referring now to FIG. 3, the topsheet 124 on the diaper 120 comprises apertured web 140. As can be seen in FIG. 3, the web 140 is only apertured in the rear or back waist region 129 of the diaper 120. The web 140 may be apertured in any suitable manner to provide the desired benefits in certain portions or regions of the diaper 120. For example, the web 140 may be apertured in only the crotch region 131 or only the front waist region 127, any combination of two regions, portions of any one region, or portions of several regions.

Figure 4:
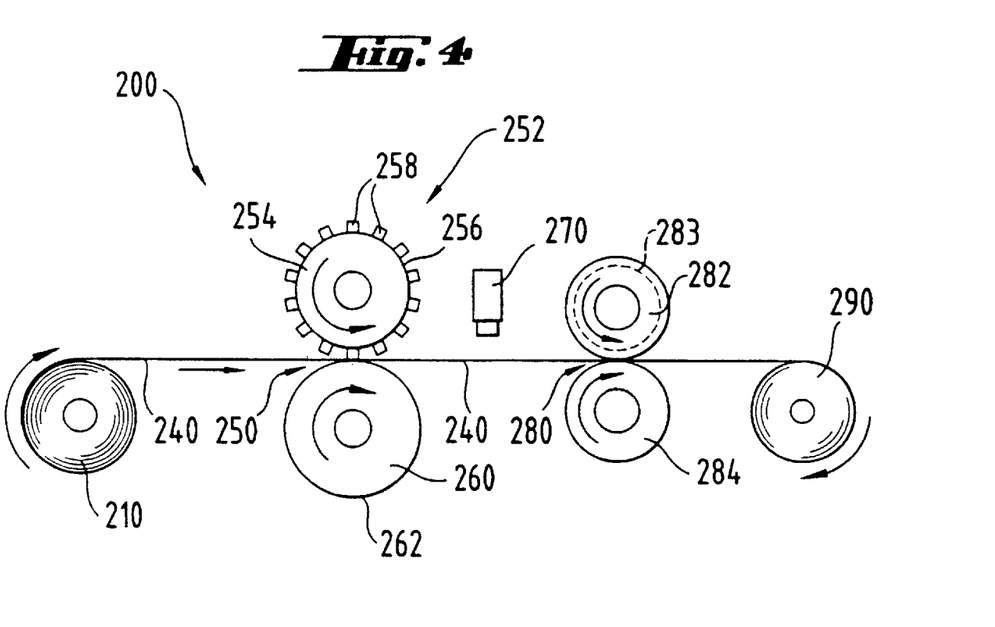
FIG. 4 is a simplified schematic illustration of a process for forming the apertured web of the present invention.

Referring now to FIG. 4 there is shown a schematic illustration of a process 200 for forming the apertured web of the present invention. A material 240 is unwound from a supply roll 210 and travels in the direction indicated by the arrows associated therewith, i.e., in the machine direction, as the supply roll 210 rotates in the direction indicated by the arrows associated therewith.

Instead of being unwound from a supply roll the material may be fed directly from a forming apparatus, e.g., a carding apparatus, a carding and calendaring apparatus, a spunbonding apparatus, a spunbonding and calendaring apparatus, a meltblowing apparatus, a meltblowing and calendaring apparatus, to the first nip 250.

The web 240 is fed through the first nip 250 of the aperturing apparatus 252 formed by rollers 254 and 260. Roller 260 has a smooth outer surface 262. Roller 260 is preferably constructed of steel. Roller 260 may be constructed of other materials, for example, rubber. Roller 254 includes a plurality of projections 258 extending about it's outer surface 256. Roller 254 is preferably constructed of steel.

Rollers 254 and 260 preferably rotate at the same velocity. While at least one of the rollers 254 and 260 is heated, preferably, both rollers 254 and 260 are heated. Preferably, roller 254 is heated to have a higher temperature than roller 260. As the web 240 passes through the first nip 250 it is apertured. As the web is apertured it is heated above its melting point such that at least a portion of the apertures perimeter is fused.

After the web 240 has been apertured by apparatus 252, the web 240 is then cooled to set the web after leaving apparatus 252. In FIG. 4, the web 240 is shown to be cooled by blowing cold air onto the web 240 from blower 270. Of course other known techniques may be used to cool the web 240. Cooling the web also solidifies the fused material extending about the perimeter of the apertures.

After cooling, the apertured web 240 is fed through the second nip 280 formed by rollers 282 and 284. Rollers 282 and 284 preferably rotate at the same velocity. Rollers 282 and 284 break the solid fused material which extends about the perimeter of the apertures. Breaking the solid fused material increases the softness of the web 240.

Figure 5:
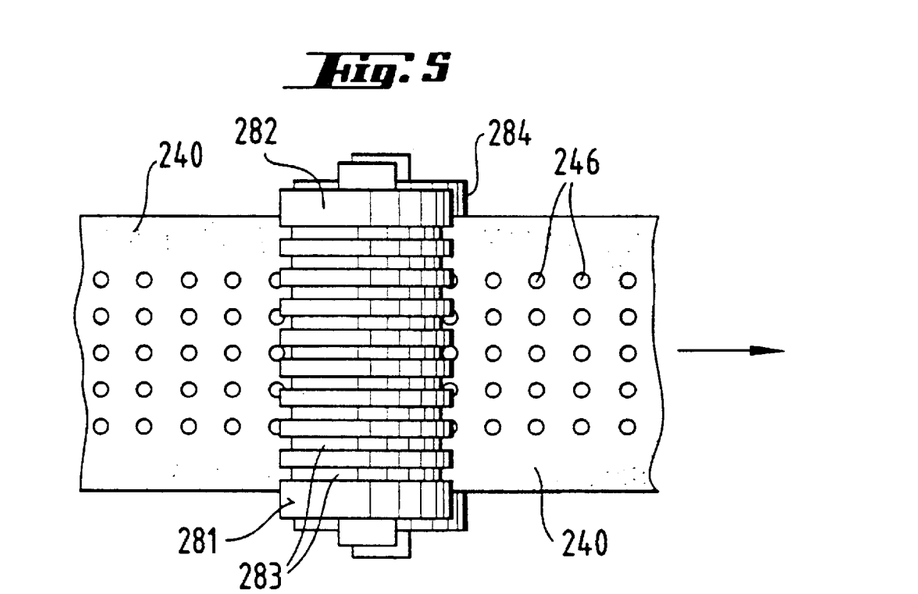
FIG. 5 is an enlarged overhead plan view illustration of the grooved roll of FIG. 4.

Roller 284 has a smooth outer surface and is preferably constructed of a soft material such as rubber, polyamide, or other polymeric material. Referring now to FIG. 5, the outer surface 281 of roller 282 comprises a plurality of grooves 283. Grooves 283 extend about the outer surface 281 in a direction parallel to the machine direction. The grooves may also extend in other directions. The size, spacing, shape and number of grooves may be selected so as to provide the desired softness in the web 240 as the grooves help to break the solid fused material which extends about the perimeter of the apertures. Roller 282 is preferably constructed of steel.

The peripheral linear speed of rollers 282 and 284 is preferably greater than the peripheral linear speed of rollers 254 and 260 thereby tensioning the material between the two sets of rollers. By adjusting the speeds of the rollers, the material is tensioned such that it necks a desired amount.

From the second nip 280 the web 240 is wound on take-up roll 290.

Figure 6:
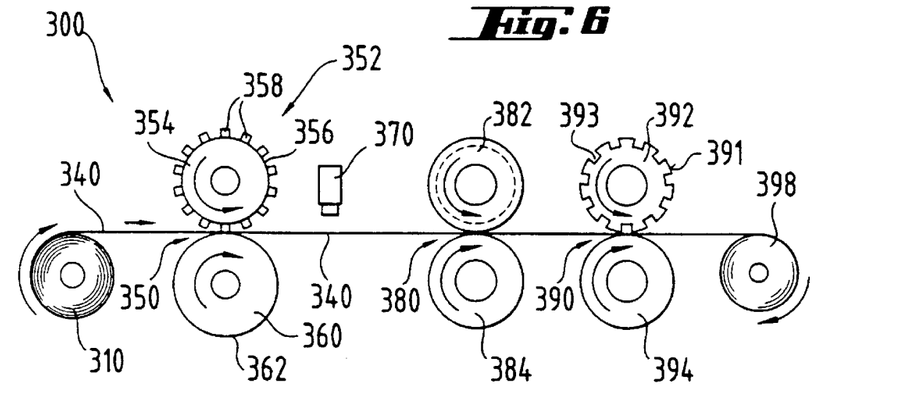
FIG. 6 is a simplified schematic illustration of another process for forming the apertured web of the present invention.

Referring now to FIG. 6, there is shown a schematic illustration of another process 300 for forming the apertured web of the present invention. A material 340 is unwound from a supply roll 310 and travels in the direction indicated by the arrows associated therewith, i.e., in the machine direction, as the supply roll 310 rotates in the direction indicated by the arrows associated therewith.

Instead of being unwound from a supply roll the material may be fed directly from a forming apparatus, e.g., a carding apparatus, a carding and calendaring apparatus, a spunbonding apparatus, a spunbonding and calendaring apparatus, a meltblowing apparatus, a meltblowing and calendaring apparatus, to the first nip 350.

The web 340 is fed through the first nip 350 of the aperturing apparatus 352 formed by rollers 354 and 360. Roller 360 has a smooth outer surface 362. Roller 360 is preferably constructed of steel. Roller 360 may be constructed of other materials, for example, rubber. Roller 354 includes a plurality of projections 358 extending about it's outer surface 356. Roller 354 is preferably constructed of steel.

Rollers 354 and 360 preferably rotate at the same velocity. While at least one of the rollers 354 and 360 is heated, preferably, both rollers 354 and 360 are heated. Preferably, roller 354 is heated to have a higher temperature than roller 360. As the web 340 passes through the first nip 350 it is apertured. As the web is apertured it is heated above its melting point such that at least a portion of the apertures perimeter is fused.

After the web 340 has been apertured by apparatus 352, the web 340 is then cooled to set the web after leaving apparatus 352. In FIG. 6, the web 340 is shown to be cooled by blowing cold air onto the web 340 from blower 370. Of course other known techniques may be used to cool the web 340. Cooling the web also solidifies the fused material extending about the perimeter of the apertures.

After cooling, the apertured web 340 is fed through the second nip 380 formed by rollers 382 and 384. Rollers 382 and 384 preferably rotate at the same velocity. Rollers 382 and 384 break the solid fused material which extends about the perimeter of the apertures. Breaking the solid fused material increases the softness of the web 340.

Roller 384 has a smooth outer surface and is preferably constructed of a soft material such as rubber, polyamide, or other polymeric material. The outer surface of roller 382 comprises a plurality of grooves. Roller 382 is the same as roller 282 shown in FIG. 5.

The peripheral linear speed of rollers 382 and 384 is preferably greater than the peripheral linear speed of rollers 354 and 360 thereby tensioning the material between the two sets of rollers. By adjusting the speeds of the rollers, the material is tensioned such that it necks a desired amount.

From the second nip 380 the web 340 is fed to the third nip 390 formed by rollers 392 and 394. Rollers 392 and 394 preferably rotate at the same velocity. Rollers 392 and 394 further break the solid fused material which extends about the perimeter of the apertures. Breaking the solid fused material increases the softness of the web 340.

Figure 7:
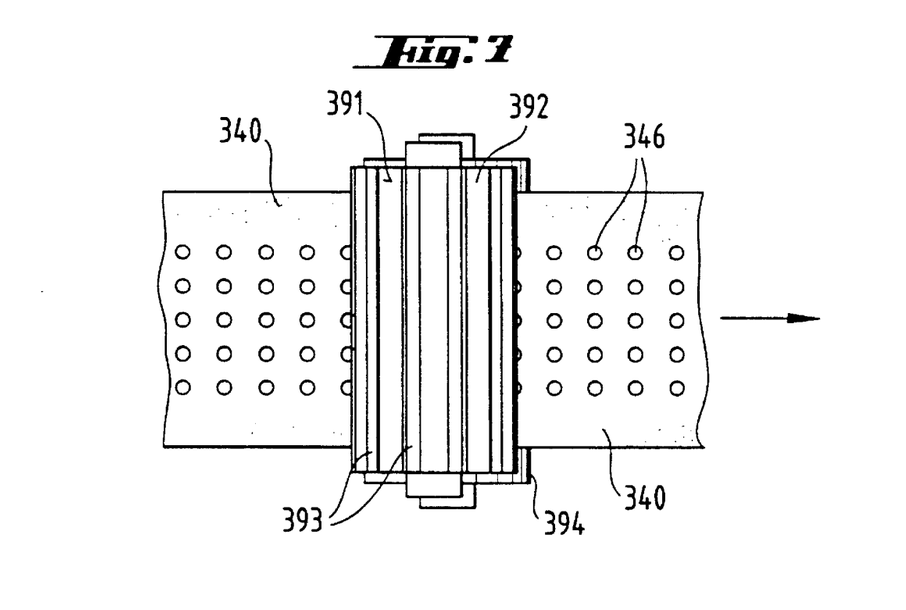
FIG. 7 is an enlarged overhead plan view illustration of the grooved roll of the third nip of FIG. 6.

Roller 394 has a smooth outer surface and is preferably constructed of a soft material such as rubber, polyamide, or other polymeric material. Referring now to FIG. 7, the outer surface 391 of roller 392 comprises a plurality of grooves 393. Grooves 393 extend about the outer surface 391 in a direction different than direction in which the grooves on roller 382 extend. Preferably, the grooves 393 extend in a direction perpendicular to the direction in which the grooves on roller 382 extend. The grooves 393 are shown in FIG. 7 to be extending in a direction perpendicular to the machine direction. The grooves may also extend in other directions. The size, spacing, shape and number of grooves may be selected so as to provide the desired softness in the web 340 as the grooves help to break the solid fused material which extends about the perimeter of the apertures. Roller 382 is preferably constructed of steel.

From the third nip 390 the web 340 is wound on take-up roll 398.

Figure 8:
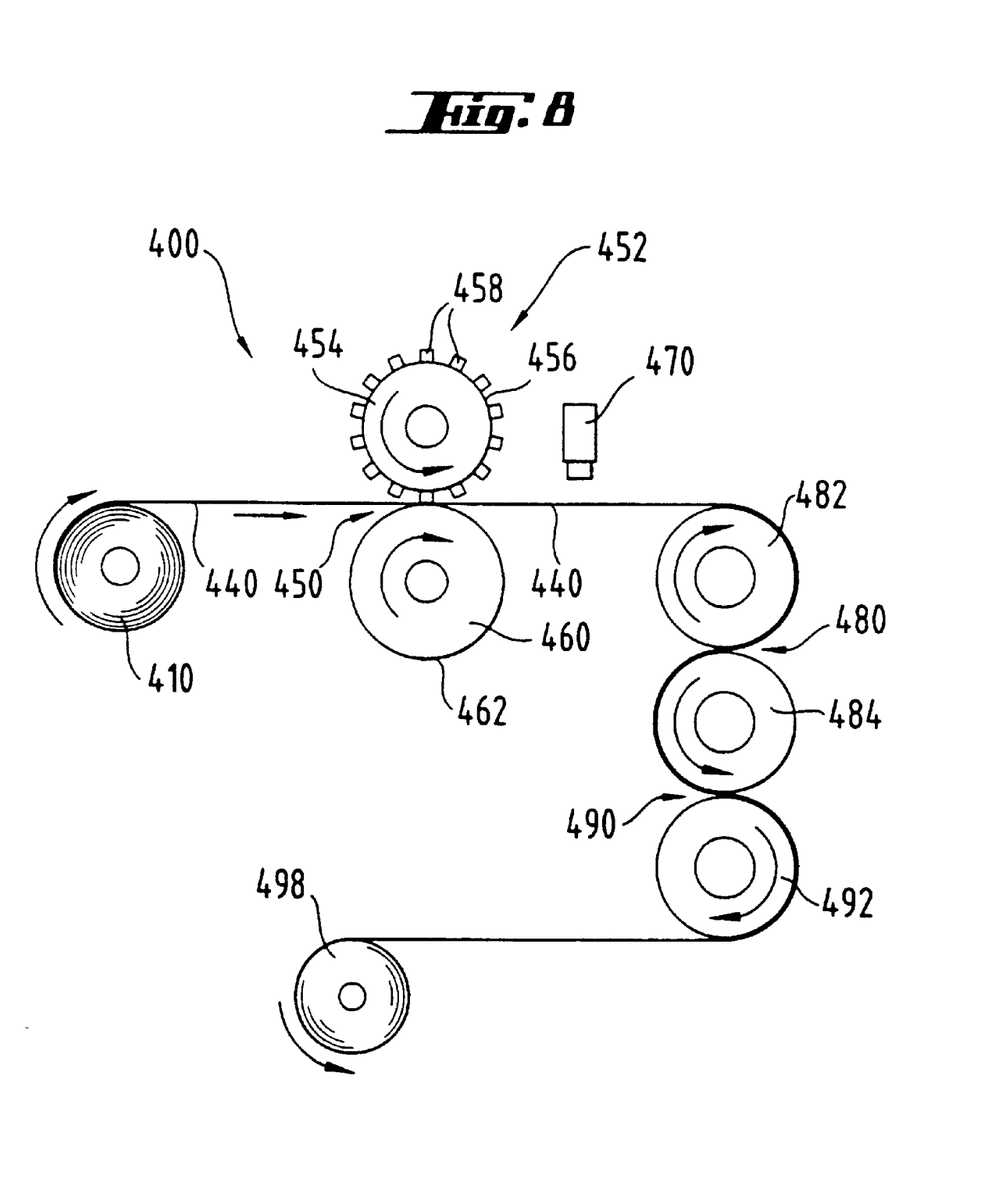
FIG. 8 is a simplified schematic illustration of another process for forming the apertured web of the present invention.

Referring now to FIG. 8, there is shown a schematic illustration of another process 400 for forming the apertured web of the present invention. The process 400 is essentially identical to the process illustrated in FIG. 6, except for the formation of the second and third nips 480 and 490. Unlike process 300 illustrated in FIG. 6, process 400 utilizes the same smooth roller 484 to form the nips 480 and 490. This simply eliminates the need for two smooth rollers. Roller 482 is identical to roller 282 illustrated in FIG. 5 and roller 492 is identical to roller 392 illustrated in FIG. 7.

Instead of feeding a single web through the processes illustrated above, multiple webs may be simultaneously fed through the processes. The webs may be identical to one another or different from one another. For example, the webs may have different hydrophilicities such that one is more hydrophilic than the other. The webs may have different dimensions such that one web is wider than the other or thicker than the other. The various combinations and number of webs which may be apertured and softened according to the present invention may be selected by the manufacturer to provide the desired results.

The diaper 20 may further comprise elasticized leg cuffs (not shown) which provide improved containment of liquids and other body exudates. Each elasticized leg cuff may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 describes a disposable diaper which provides a contractible leg opening having a side flap and one or more elastic members to provide an elasticized leg cuff (gasketing cuff). Commonly assigned U.S. Pat. No. 4,909,803 entitled "Disposable Absorbent Article Having Elasticized Flaps" issued to Aziz et al. on Mar. 20, 1990, describes a disposable diaper 20 having "stand-up" elasticized flaps (barrier cuffs) to improve the containment of the leg regions. Commonly assigned U.S. Pat. No. 4,695,278 entitled "Absorbent Article Having Dual Cuffs" issued to Lawson on Sep. 22, 1987, describes a disposable diaper 20 having dual cuffs including a gasketing cuff and a barrier cuff.

The diaper 20 preferably further comprises an elastic waist feature (not shown) that provides improved fit and containment. The elastic waist feature is that portion or zone of the diaper 20 which is intended to elastically expand and contract to dynamically fit the wearer's waist. The elastic waist feature at least extends longitudinally outwardly from at least one of the waist edges of the absorbent core 28 and generally forms at least a portion of the end edge of the diaper 20. Disposable diapers are generally constructed so as to have two elastic waist features, one positioned in the first waist region 27 and one positioned in the second waist region 29, although diapers can be constructed with a single elastic waist feature. Further, while the elastic waist feature or any of its constituent elements can comprise a separate element affixed to the diaper 20, the elastic waist feature is preferably constructed as an extension of other elements of the diaper 20 such as the backsheet 26 or the topsheet 24, preferably both the backsheet 26 and the topsheet 24. The elasticized waistband may be constructed in a number of different configurations including those described in U.S. Pat. No. 4,515,595 issued to Kievit et al. on May 7, 1985 and the above referenced U.S. patent application Ser. No. 07/715,152; each of these references being incorporated herein by reference.

The diaper 20 also comprises a fastening system 36 which forms a side closure which maintains the first waist region 27 and the second waist region 29 in an overlapping configuration such that lateral tensions are maintained around the circumference of the diaper 20 to maintain the diaper 20 on the wearer. Exemplary fastening systems are disclosed in U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; commonly assigned U.S. Pat. No. 4,946,527 entitled "Pressure-Sensitive Adhesive Fastener And Method of Making Same" issued to Battrell on Aug. 7, 1990; commonly assigned U.S. Pat. No. 3,848,594 entitled "Tape Fastening System for Disposable Diaper" issued to Buell on Nov. 19, 1974; commonly assigned U.S. Patent B1 4,662,875 entitled "Absorbent Article" issued to Hirotsu et al. on May 5, 1987; and the hereinbefore referenced U.S. patent application Ser. No. 07/715,152; each of which is incorporated herein by reference.

The diaper 20 is preferably applied to a wearer by positioning one of the waist regions, preferably the second waist region 29, under the wearer's back and drawing the remainder of the diaper 20 between the wearer's legs so that the other waist region, preferably the first waist region 27, is positioned across the front of the wearer. The tape tabs 36 of the fastening system are then released from the release portion. The diaperer then wraps the elasticized side panel around the wearer, while still grasping the tab portion. The fastening system is secured to the outer surface of the diaper 20 to effect two side closure.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of forming an apertured web, said method comprising the steps of:
   a) feeding a web in a machine direction through a first nip formed by a pair of rollers one of said rollers having a smooth outer surface and the other roller having an outer surface with a plurality of projections extending from said outer surface, at least one of said rollers being heated, such that said web is apertured with a plurality of apertures with the web removed and a fuse perimeter;
   b) cooling said web to solidify said fused perimeter of said apertures; and
   c) feeding said web through a second nip formed by a pair of rollers to break said solidified fused perimeter of said apertures, one of said rollers of said second nip having an outer surface with a plurality of grooves.

2. The method of claim 1 comprising the additional step of:
   d) feeding said web through a third nip formed by a pair of rollers to break said solidified fused perimeter of said apertures, one of said rollers of said third nip having an outer surface with a plurality of grooves.

3. The method of claim 2 wherein said plurality of grooves on said outer surface of said roller forming said second nip extend in a first direction and said plurality of grooves on said outer surface of said roller forming said third nip extend a direction different from said first direction.

4. The method of claim 3 wherein said first direction is parallel to said machine direction.

5. The method of claim 1 wherein said web comprises a nonwoven web.

6. The method of claim 1 wherein a second web is simultaneously fed through said first and second nips.

7. The method of claim 1 wherein the web is cooled by blowing cool air onto the web.

8. The method of claim 1 wherein one of said rollers forming said second nip has a smooth outer surface.

9. The method of claim 2 wherein one of said rollers forming said third nip has a smooth outer surface.

* * * * *